(12) United States Patent
Baileykobayashi et al.

(10) Patent No.: US 11,339,203 B2
(45) Date of Patent: May 24, 2022

(54) ANTITUMOR PEPTIDE AND USE THEREOF

(71) Applicants: TOAGOSEI CO., LTD., Tokyo (JP); National University Corporation Nagoya University, Aichi-ken (JP)

(72) Inventors: Nahoko Baileykobayashi, Ibaraki-ken (JP); Tetsuhiko Yoshida, Ibaraki-ken (JP); Makoto Sawada, Aichi-ken (JP)

(73) Assignees: Toagosei Co., Ltd., Tokyo (JP); National University Corporation Nagoya University, Aichi-Ken (JP)

( * ) Notice: Subject to any disclaimer, the term of this patent is extended or adjusted under 35 U.S.C. 154(b) by 0 days.

(21) Appl. No.: 16/525,781

(22) Filed: Jul. 30, 2019

(65) Prior Publication Data

US 2020/0031902 A1   Jan. 30, 2020

(30) Foreign Application Priority Data

Jul. 30, 2018  (JP) .............................. JP2018-142265

(51) Int. Cl.
| | | |
|---|---|---|
| *C07K 14/705* | (2006.01) |
| *C07K 14/47* | (2006.01) |
| *A61P 35/00* | (2006.01) |
| *A61K 38/00* | (2006.01) |

(52) U.S. Cl.
CPC ........ *C07K 14/70596* (2013.01); *A61P 35/00* (2018.01); *C07K 14/47* (2013.01); *A61K 38/00* (2013.01); *C07K 2319/03* (2013.01)

(58) Field of Classification Search
None
See application file for complete search history.

(56) References Cited

U.S. PATENT DOCUMENTS

| | | | | |
|---|---|---|---|---|
| 2008/0260719 A1* | 10/2008 | Liao | ................. | G01N 33/56972 424/130.1 |
| 2012/0165507 A1* | 6/2012 | Jazayeri-Dezfuly | ......................... | C07K 14/705 530/350 |
| 2018/0141985 A1* | 5/2018 | Baileykobayashi | ... | C07K 14/47 |

OTHER PUBLICATIONS

Mahajan et. al. "Sphingosine 1-Phosphate (S1P) Signaling in Glioblastoma Multiforme—A Systematic Review", International Journal of Molecular Sciences, 2017, 18, 2448.
Pyne et. al. "Sphingosine 1-phosphate and cancer" Nature Reviews, 2010, 10, 489-503.
Davis, et. al. "Sphingosine 1-Phosphate Analogs as Receptor Antagonists", The Journal of Biological Chemistry, 2005, 280, 9833-9841.
Sanna et. al. "Enhancement of capillary leakage and restoration of lymphocyte egress by a chiral S1P1 antagonist in vivo", Nature Chemical Biology, 2006, 1-8.
Hirata et. al. "Sphingosine-1-phosphate promotes expansion of cancer stem cells via S1PR3 by a ligand-independent Notch activation", Nature Communications, 2014, 1-14.
Shimizu, Yoshihiro, et al. "Cell-free translation reconstituted with purified components." Nature biotechnology 19.8 (2001): 751.-755.
Madin, Kairat, et al. "A highly efficient and robust cell-free protein synthesis system prepared from wheat embryos: plants apparently contain a suicide system directed at ribosomes." Proceedings of the National Academy of Sciences 97.2 (2000): 559-564.

* cited by examiner

*Primary Examiner* — Maury A Audet
(74) *Attorney, Agent, or Firm* — Meunier Carlin & Curfman LLC

(57) ABSTRACT

The antitumor peptide provided by the present invention is a synthetic peptide including both of:
(1) an amino acid sequence composing the second transmembrane region from the N-terminal of a membrane protein sphingosine 1-phosphate receptor 1 (S1PR1), or a modified amino acid sequence formed by deletion substitution or addition of 1, 2 or 3 amino acid residues in the amino acid sequence; and
(2) an amino acid sequence functioning as a cell-penetrating peptide (CPP); wherein
the total number of amino acid residues is 100 or less.

4 Claims, No Drawings

Specification includes a Sequence Listing.

SEQUENCE LISTING

<160> NUMBER OF SEQ ID NOS: 33

<210> SEQ ID NO 1
<211> LENGTH: 22
<212> TYPE: PRT
<213> ORGANISM: Artificial Sequence

```
<220> FEATURE:
<223> OTHER INFORMATION: Synthetic peptide

<400> SEQUENCE: 1

Leu Thr Ser Val Val Phe Ile Leu Ile Cys Cys Phe Ile Ile Leu Glu
1               5                   10                  15

Asn Ile Phe Val Leu Leu
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic peptide

<400> SEQUENCE: 2

Phe Ile Gly Asn Leu Ala Leu Ser Asp Leu Leu Ala Gly Val Ala Tyr
1               5                   10                  15

Thr Ala Asn Leu Leu Leu
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide

<400> SEQUENCE: 3

Trp Phe Leu Arg Glu Gly Ser Met Phe Val Ala Leu Ser Ala Ser Val
1               5                   10                  15

Phe Ser Leu Leu Ala Ile
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

Phe Leu Leu Ile Ser Ala Cys Trp Val Ile Ser Leu Ile Leu Gly Gly
1               5                   10                  15

Leu Pro Ile Met Gly Trp
            20

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide

<400> SEQUENCE: 5

Leu Tyr His Lys His Tyr Ile Leu Phe Cys Thr Thr Val Phe Thr Leu
1               5                   10                  15

Leu Leu Leu Ser Ile Val Ile Leu Tyr Cys Arg Ile
            20                  25

<210> SEQ ID NO 6
<211> LENGTH: 21
<212> TYPE: PRT
```

```
<213> ORGANISM: Artificial Sequence
<220> FEATURE:
<223> OTHER INFORMATION: Synthetic peptide

<400> SEQUENCE: 6

Val Ile Ile Val Leu Ser Val Phe Ile Ala Cys Trp Ala Pro Leu Phe
1               5                   10                  15

Ile Leu Leu Leu
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic peptide

<400> SEQUENCE: 7

Leu Phe Arg Ala Glu Tyr Phe Leu Val Leu Ala Val Leu Asn Ser Gly
1               5                   10                  15

Thr Asn Pro Ile Ile
            20

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide

<400> SEQUENCE: 8

Arg Ser Arg Lys Tyr Thr Ser Trp Tyr Val Ala Leu Lys Arg
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Met Ala Lys Ser Ile Arg Ser Lys His Arg Arg Gln Met Arg Met Met
1               5                   10                  15

Lys Arg

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Met Ala Arg Arg Arg Arg His Arg Gly Pro Arg Arg Pro Arg Pro Pro
1               5                   10                  15

<210> SEQ ID NO 11
<211> LENGTH: 19
<212> TYPE: PRT
<213> ORGANISM: Artificial Sequence
<220> FEATURE:
<223> OTHER INFORMATION: Synthetic peptide

<400> SEQUENCE: 11
```

```
Gly Arg Cys Arg Arg Leu Ala Asn Phe Gly Pro Arg Lys Arg Arg
1               5                   10                  15

Arg Arg Arg

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Arg Arg Arg Lys Arg Asn Arg Asp Ala Arg Arg Arg Arg Lys Gln
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide

<400> SEQUENCE: 13

Met Gln Arg Lys Pro Thr Ile Arg Arg Lys Asn Leu Arg Leu Arg Arg
1               5                   10                  15

Lys

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Ile Met Arg Arg Arg Gly Leu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Lys Lys Leu Lys Lys Arg Asn Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Arg Arg Arg Ala Asn Asn Arg Arg Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 17

Arg Lys Lys Arg Lys Lys Lys
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Lys Arg Lys Gly Lys Leu Lys Asn Lys Gly Ser Lys Arg Lys Lys
1               5                   10                  15

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Ser Lys Arg Leu Ser Ser Arg Ala Arg Lys Arg Ala Ala Lys Arg Arg
1               5                   10                  15

Leu Gly

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide

<400> SEQUENCE: 20

Lys Arg Pro Arg Arg Pro Ser Arg Pro Phe Arg Lys Pro
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic peptide

<400> SEQUENCE: 21

Lys Lys Arg Thr Leu Arg Lys Asn Asp Arg Lys Lys Arg
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Trp Arg Arg Gln Ala Arg Phe Lys
1               5

<210> SEQ ID NO 23
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 23

Arg Lys Lys Arg Arg Gln Arg Arg Arg
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Tyr Ala Arg Ala Ala Ala Arg Gln Ala Arg Ala
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide

<400> SEQUENCE: 25

Lys Gly Arg Gln Val Lys Val Trp Phe Gln Asn Arg Arg Met Lys Trp
1               5                   10                  15

Lys Lys

<210> SEQ ID NO 26
<211> LENGTH: 35
<212> TYPE: PRT
<213> ORGANISM: Artificial Sequence
<220> FEATURE:
<223> OTHER INFORMATION: Synthetic peptide

<400> SEQUENCE: 26

Leu Thr Ser Val Val Phe Ile Leu Ile Cys Cys Phe Ile Ile Leu Glu
1               5                   10                  15

Asn Ile Phe Val Leu Leu Lys Lys Arg Thr Leu Arg Lys Asn Asp Arg
            20                  25                  30

Lys Lys Arg
        35

<210> SEQ ID NO 27
<211> LENGTH: 35
<212> TYPE: PRT
<213> ORGANISM: Artificial Sequence
<220> FEATURE:
<223> OTHER INFORMATION: Synthetic peptide

<400> SEQUENCE: 27

Phe Ile Gly Asn Leu Ala Leu Ser Asp Leu Leu Ala Gly Val Ala Tyr
1               5                   10                  15

Thr Ala Asn Leu Leu Leu Lys Lys Arg Thr Leu Arg Lys Asn Asp Arg
            20                  25                  30

Lys Lys Arg
        35

<210> SEQ ID NO 28
<211> LENGTH: 35
<212> TYPE: PRT
<213> ORGANISM: Artificial Sequence
<220> FEATURE:
```

<223> OTHER INFORMATION: Synthetic peptide

<400> SEQUENCE: 28

Trp Phe Leu Arg Glu Gly Ser Met Phe Val Ala Leu Ser Ala Ser Val
1               5                   10                  15

Phe Ser Leu Leu Ala Ile Lys Lys Arg Thr Leu Arg Lys Asn Asp Arg
            20                  25                  30

Lys Lys Arg
        35

<210> SEQ ID NO 29
<211> LENGTH: 35
<212> TYPE: PRT
<213> ORGANISM: Artificial Sequence
<220> FEATURE:
<223> OTHER INFORMATION: Synthetic peptide

<400> SEQUENCE: 29

Phe Leu Leu Ile Ser Ala Cys Trp Val Ile Ser Leu Ile Leu Gly Gly
1               5                   10                  15

Leu Pro Ile Met Gly Trp Lys Lys Arg Thr Leu Arg Lys Asn Asp Arg
            20                  25                  30

Lys Lys Arg
        35

<210> SEQ ID NO 30
<211> LENGTH: 41
<212> TYPE: PRT
<213> ORGANISM: Artificial Sequence
<220> FEATURE:
<223> OTHER INFORMATION: Synthetic peptide

<400> SEQUENCE: 30

Leu Tyr His Lys His Tyr Ile Leu Phe Cys Thr Thr Val Phe Thr Leu
1               5                   10                  15

Leu Leu Leu Ser Ile Val Ile Leu Tyr Cys Arg Ile Lys Lys Arg Thr
            20                  25                  30

Leu Arg Lys Asn Asp Arg Lys Lys Arg
        35                  40

<210> SEQ ID NO 31
<211> LENGTH: 34
<212> TYPE: PRT
<213> ORGANISM: Artificial Sequence
<220> FEATURE:
<223> OTHER INFORMATION: Synthetic peptide

<400> SEQUENCE: 31

Val Ile Ile Val Leu Ser Val Phe Ile Ala Cys Trp Ala Pro Leu Phe
1               5                   10                  15

Ile Leu Leu Leu Leu Lys Lys Arg Thr Leu Arg Lys Asn Asp Arg Lys
            20                  25                  30

Lys Arg

<210> SEQ ID NO 32
<211> LENGTH: 34
<212> TYPE: PRT
<213> ORGANISM: Artificial Sequence
<220> FEATURE:
<223> OTHER INFORMATION: Synthetic peptide

<400> SEQUENCE: 32

```
Leu Phe Arg Ala Glu Tyr Phe Leu Val Leu Ala Val Leu Asn Ser Gly
1               5                   10                  15

Thr Asn Pro Ile Ile Lys Lys Arg Thr Leu Arg Lys Asn Asp Arg Lys
            20                  25                  30

Lys Arg

<210> SEQ ID NO 33
<211> LENGTH: 31
<212> TYPE: PRT
<213> ORGANISM: Artificial Sequence
<220> FEATURE:
<223> OTHER INFORMATION: Synthetic peptide

<400> SEQUENCE: 33

Phe Ile Gly Asn Leu Ala Leu Ser Asp Leu Leu Ala Gly Val Ala Tyr
1               5                   10                  15

Thr Ala Asn Leu Leu Arg Lys Lys Arg Arg Gln Arg Arg
            20                  25                  30
```

ANTITUMOR PEPTIDE AND USE THEREOF

CROSS-REFERENCE TO RELATED APPLICATIONS

The present application claims the benefit of priority based on Japanese Patent Application No. 2018-142265 filed on Jul. 30, 2018, which is incorporated by reference in its entirety.

TECHNICAL FIELD

The present invention relates to an artificially synthesized antitumor peptide capable of suppressing proliferation of tumor cells and to the use thereof. More particularly, the present invention relates to the use of an artificial peptide provided with an amino acid sequence (also referred to as a "TM sequence") comprising a transmembrane (TM) region of a sphingosine 1-phosphate receptor 1 (S1PR1) and a cell-penetrating peptide sequence.

TECHNICAL BACKGROUND

There have been numerous reports in recent years stating that sphingosine 1-phosphate (S1P), a constituent component of cell membrane, promotes cancer exacerbation. SIP level is higher in serum of cancer patients than in healthy individuals, and expression of SIP synthase, sphingosine kinase 1 (SphK1), and receptor S1PR have also been reported to be elevated in cancer patients. In vitro, S1P has been reported to promote proliferation and metastasis of tumor cells as well as promote inflammation and vascularization in tumor microenvironment, thereby providing favorable conditions for tumor growth. Consequently, S1P and S1PR can become new treatment targets in cancer therapy. Recently developed S1PR inhibitors are greatly expected to express anti-cancer activity. Refer to, for example, the report by Mahajan-Thakur, et al. (Mahajan-Thakur, et al., International Journal of Molecular Sciences, 2017, 18, 2448), the report by Pyne, et al. (Nigel J. Pyne and Susan Pyne, Nature Reviews, 2010, 10, 489-503), and the report of Davis, et al. (Davis, et al., The Journal of Biological Chemistry, 2005, 280, 9833-9841).

SUMMARY OF THE INVENTION

Meanwhile, research has been also rapidly progressing on treatment targeted at disease-specific molecules, and numerous molecule-targeting therapeutic drugs have been developed, including antibody drugs. An example of molecule-targeting therapy for cancer is drug therapy against epidermal growth factor receptor 2(EGFR2, also refer to as Her2)-positive breast cancer using anti-Her2 antibody. Although molecule-targeting therapeutic drugs exert superior antitumor action against targeted cancer, they are either ineffective or exhibit extremely low efficacy against cancer that does not express target antigen of the drug. For example, although treatment using anti-Her2 antibody exerts therapeutic efficacy against Her2-expressing breast cancer, it is not selected for treatment against breast cancer patients not expressing Her2.

In addition, antitumor drugs using an antibody as an active ingredient thereof are very expensive, which can cause unavoidable serious cost problems in cancer treatment.

With this in mind, the present invention was created to provide synthetic peptides which have different antitumor (anticancer) mechanism and composition from expensive antitumor drugs using antibodies.

The inventors of the present invention focused in particular on TM region of seven-pass transmembrane protein, S1PR1, expressed in mammals (SEQ ID NOS: 1 to 7). And surprisingly, the inventors of the present invention found that synthetic peptides combining an amino acid sequence composing the second TM region from the N-terminal of S1PR1 (SEQ ID NO: 2) and an amino acid sequence composing a conventionally known cell penetrating peptide (CPP) in particular has superior antitumor activity (anticancer activity) against various tumor cells, thereby leading to completion of the present invention.

Namely, the synthetic peptide disclosed herein is an antitumor peptide capable of suppressing proliferation of at least one type of tumor cells. This peptide is characterized by comprising the amino acid sequences indicated in following (1) and (2):

(1) an amino acid sequence composing a seven-pass transmembrane protein S1PR1, and particularly an amino acid sequence composing the second TM region from the N-terminal of the protein, or a modified amino acid sequence formed by deletion, substitution or addition of 1, 2, or 3 amino acid residues in the amino acid sequence; and (2) an amino acid sequence functioning as a cell-penetrating peptide (CPP).

In a preferable aspect thereof, the antitumor peptide disclosed herein has total 100 or fewer amino acid residues. The total number of amino acid residues is more preferably 80 or less (such as 70 or less) from the viewpoints of production cost, easy synthesis and handling.

Alternatively, a synthetic peptide in which the amino acid sequence indicated in (1) above and the amino acid sequence indicated in (2) above account for 80% or more (and more preferably 90% or more, and for example, 100%) of the amino acid sequences of the entire peptide is a particularly preferably aspect of the antitumor peptide disclosed herein.

In another preferable aspect of the antitumor peptide disclosed herein, the amino acid sequence composing the TM region of S1PR1 is particularly preferably characterized by being the amino acid sequence represented by SEQ ID NO: 2 that composes the second TM region from the N-terminal of the protein.

In another preferable aspect of the antitumor peptide disclosed herein, the amino acid sequence functioning as a CPP is characterized by being polyarginine (typically composed of 5 to 9 arginine residues although not particularly limited thereto), an amino acid sequence represented by any of SEQ ID NOS: 8 to 25, or a modified amino acid sequence formed by deletion, substitution or addition of 1, 2, or 3 amino acid residues in the amino acid sequence.

For example, a preferable example thereof is a synthetic peptide provided with both of:

(i) the amino acid sequence represented by SEQ ID NO: 2 or a modified amino acid sequence formed by deletion, substitution or addition of 1, 2, or 3 amino acid residues in the amino acid sequence; and (ii) polyarginine, an amino acid sequence represented by any one of SEQ ID NOS: 8 to 25, or a modified amino acid sequence formed by deletion, substitution or addition of 1, 2, or 3 amino acid residues in the amino acid sequence.

In another preferable aspect of the antitumor peptide disclosed herein, the sequence functioning as a CPP (or a modified amino acid sequence thereof) is arranged directly adjacent to each other, or via 10 or fewer (and preferably 5 or less, such as 1 or 2) amino acid residues functioning as a linker, to the N-terminal or C-terminal of the amino acid sequence composing the second TM region from the N-terminal of 51PR1 (or a modified amino acid sequence thereof).

In a preferable aspect thereof, the antitumor peptide disclosed herein is characterized by having an amino acid sequence represented by SEQ ID NO: 27 or SEQ ID NO: 33.

In addition, the present invention provides an antitumor composition suppressing proliferation of at least one type of tumor cells, the antitumor composition comprising any of the synthetic peptides (antitumor peptides) disclosed herein and at least one pharmacologically acceptable carrier.

This composition can be used as an antitumor drug (including an anticancer drug; the same applies hereinafter) by containing the antitumor peptide disclosed herein or as a material for developing a novel antitumor drug.

In addition, the present invention provides a method for suppressing proliferation of at least one type of tumor cells, comprising supplying the synthetic peptide (antitumor peptide) disclosed herein at least once to target tumor cells (either in vitro or in vivo).

In the method employing this configuration, proliferation of the tumor cells (and thus an increase in tumor or cancer tissue) can be inhibited or suppressed by supplying the antitumor peptide disclosed herein to tumor cells.

DESCRIPTION OF THE RELATED EMBODIMENTS

The following provides an explanation of preferred embodiments of the present invention. Matters that are required to carry out the present invention (such as chemical synthesis methods of peptides, cell culturing methods or general matters relating to the preparation of a pharmaceutical composition containing a peptide as a component thereof) except the matters not specifically mentioned in the present description (such as the primary structure or chain length of the synthetic peptide disclosed herein) can be understood as design matters for people with ordinary skill in the art on the basis of conventional technologies in fields such as cell engineering, physiology, medicine, pharmacology, organic chemistry, biochemistry, genetic engineering, protein engineering, molecular biology or genetics. The present invention can be carried out on the basis of the contents disclosed in the present description and common general technical knowledge in the relevant art. Furthermore, in the following explanation, amino acids are represented with a single character (although three-character notation is used in the sequence listings).

The entirety of all documents cited in the present description are incorporated in the present description by reference.

In the present description, "tumor" is a term interpreted in broad sense of the word, and refers to tumors in general (and typically, malignant tumors) including carcinomas, sarcomas or hematomas and lesions of blood or hematopoietic tissue (such as leukemia or lymphoma). In addition, "tumor cells" has the same meaning as "cancer cells", and refers to cells that form such tumor that have typically undergone abnormal proliferation unrelated to surrounding normal tissue (so-called cancerous cells). Thus, unless specifically defined otherwise, if cells are cells that are not normal cells, but rather are classified as tumor cells (cancer cells), that cells are referred to as tumor cells regardless of the origin or properties thereof. Cells composing epithelial tumors (such as squamous cell carcinoma or adenoma), non-epithelial tumors (such as various types of sarcoma or osteosarcoma), various types of cell cytomas (such as neuroblastoma or retinoblastoma), lymphomas or melanomas and the like are typical examples of cells included in tumor cells as referred to here.

In addition, in the present description, a "synthetic peptide" refers to a peptide fragment created by artificial chemical synthesis or biosynthesis (namely, produced based on genetic engineering) in which a peptide chain thereof is independently and stably present in nature alone, but rather is able to be stably present in a prescribed composition. Here, "peptide" is a term indicating an amino acid polymer having a plurality of peptide bond, and refers to that which, although not limited by the number of amino acid residues contained in the peptide chain, typically has a comparatively small molecular weight in which the total number of amino acid residues is typically roughly 100 or less (preferably 80 or less, more preferably 70 or less, and particularly preferably 50 or less).

In addition, in the present description, "amino acid residue" is a term that includes the N-terminal amino acid and C-terminal amino acid of a peptide chain, excluding cases in which this is specifically indicated otherwise.

Furthermore, in the amino acid sequences described in the present description, the left side is always the N-terminal side and the right side is always the C-terminal side.

In the present description, "modified amino acid sequence" with respect to a prescribed amino acid sequence refers to an amino acid sequence formed by substituting, deleting or adding (inserting) 1 or more (typically 9 or less and preferably 5 or less) of amino acid residues, such as 1, 2, or 3 amino acid residues, without impairing the function possessed by that prescribed amino acid sequence (such as antitumor activity or cell membrane permeability). For example, a sequence obtained by so-called conservative amino acid replacement of 1, 2 or 3 amino acid residues (for example, sequences having basic amino acid residues substituted for other basic amino acid residues, such as mutual substitution of lysine and arginine residues), and sequences obtained by adding (inserting) or deleting 1, 2 or 3 amino acid residues in a given amino acid sequence. Thus, the antitumor peptides disclosed herein as examples of the present invention include not only synthetic peptides comprising modified amino acid sequences formed by substituting (typically by conservative substitution), deleting or adding 1, 2 or 3 amino acid residues in the amino acid sequences of the sequence ID numbers, and exhibiting antitumor activity equivalent to that of the amino acid sequences of these sequence ID numbers.

The artificially synthesized antitumor peptide disclosed herein is a short chain peptide that does not exist in nature that is characterized by being provided with both above-mentioned 2 types of amino acid sequences, namely:

(1) an amino acid sequence composing the second TM region from the N-terminal of S1PR1 represented by SEQ ID NO: 2, or a modified amino acid sequence formed by deletion, substitution or addition of 1, 2, or 3 amino acid residues in the amino acid sequence; and (2) an amino acid sequence functioning as a CPP.

S1PR1 is a G protein-coupled receptor typically composed of about 382 amino acid residues, and activates intracellular signaling pathway interacting with a ligand S1P. According to above-mentioned reports by Mahajan-Thakur, et al. and Pyne, et al., proliferation and mobility of cancer cells are accelerated by S1P-S1PR1 interaction. In addition, as is indicated in above-mentioned report by Davis, et al., compounds inhibiting S1PR have been studied. Clinically speaking, S1PR1 and S1PR3 agonist FTY720 has been approved as a drug for treatment against multiple sclerosis and is expected to be applied to cancer treatment.

However, the second TM region from the N-terminal of S1PR1 have not been found to have antitumor activity, and obtaining an artificially synthesized antitumor peptide by synthesizing the amino acid sequence of the second TM region from the N-terminal and adding CPP to the amino acid sequence have not been conceived of whatsoever at the time of filing of the present application.

Genes encoding S1PR1 (including the case of being cDNA) have been found in mammals such as humans, mice, rats, cows, cats, and Rhesus monkeys as well as in birds such as chickens. S1PR1 gene data and amino acid sequence data can be acquired by accessing the public knowledge bases (databases) of various international institutions. For example, the complete amino acid sequence of S1PR1 having various biological origins along with amino acid sequence data on the TM region can be obtained from Universal Protein Resource (UniProt).

SEQ ID NO: 2 indicates the amino acid sequence that composes the second TM region from the N-terminal of S1PR1. More specifically, this sequence is a sequence originating in humans, mice, rats, cows, cats, and Rhesus monkeys. The sequence of the second TM region from the N-terminal of S1PR1 is conserved among these animal species.

Various conventionally known CPP can be employed for the amino acid sequence functioning as a CPP used to construct the antitumor peptide disclosed herein. For example, so-called polyarginine (Rn), which is composed of 3 or more or preferably 5 or more and 11 or less or preferably 9 or less arginine residues, is preferable for the CPP used herein. In addition thereto, various other known CPP can also be employed.

Preferable examples of CPP are shown in SEQ ID NOS: 8 to 25, although not particularly limited thereto. More specifically, these examples are as indicated below.

The amino acid sequence represented by SEQ ID NO: 8 corresponds to a nucleolar localization signal (NoLS) composed of total 14 amino acid residues derived from basic fibroblast growth factor (FGF2).

The amino acid sequence represented by SEQ ID NO: 9 corresponds to an NoLS composed of total 19 amino acid residues derived from one type of nucleolar protein (ApLLP).

The amino acid sequence represented by SEQ ID NO: 10 corresponds to an NoLS composed of total 16 amino acid residues derived from (γ(1)34.5) protein of herpes simplex virus type 1 (HSV-1).

The amino acid sequence represented by SEQ ID NO: 11 corresponds to an NoLS composed of total 19 amino acid residues derived from p40 protein of human I-mfa domain-containing protein (HIC).

The amino acid sequence represented by SEQ ID NO: 12 corresponds to an NoLS composed of total 16 amino acid residues derived from MEQ protein of Marek's disease virus (MDV).

The amino acid sequence represented by SEQ ID NO: 13 corresponds to an NoLS composed of total 17 amino acid residues derived from Survivin-delta Ex3, protein that suppresses apoptosis.

The amino acid sequence represented by SEQ ID NO: 14 corresponds to an NoLS composed of total 7 amino acid residues derived from vascular growth factor, angiogenin.

The amino acid sequence represented by SEQ ID NO: 15 corresponds to an NoLS composed of total 8 amino acid residues derived from MDM2, a nuclear phosphoprotein that forms complex with p53 tumor suppressor protein.

The amino acid sequence represented by SEQ ID NO: 16 corresponds to an NoLS composed of total 9 amino acid residues derived from betanodavirus protein, GGNNVα.

The amino acid sequence represented by SEQ ID NO: 17 corresponds to an NoLS composed of total 7 amino acid residues derived from NF-κB-inducing kinase (NIK).

The amino acid sequence represented by SEQ ID NO: 18 corresponds to an NoLS composed of total 15 amino acid residues derived from nuclear VCP-like protein.

The amino acid sequence represented by SEQ ID NO: 19 corresponds to an NoLS composed of total 18 amino acid residues derived from nucleolar protein, p120.

The amino acid sequence represented by SEQ ID NO: 20 corresponds to an NoLS composed of total 14 amino acid residues derived from ORF57 protein of herpes virus saimiri (HVS).

The amino acid sequence represented by SEQ ID NO: 21 corresponds to an NoLS composed of total 13 amino acid residues extending from the 491st amino acid residue to the 503rd amino acid residue of LIM kinase 2 present in human endothelial cells, one type of protein kinase involved in intracellular signal transduction.

The amino acid sequence represented by SEQ ID NO: 22 corresponds to an NoLS composed of total 8 amino acid residues contained in nucleocapsid protein (N protein) of avian infectious bronchitis virus (IBV).

The amino acid sequence represented by SEQ ID NO: 23 corresponds to a membrane-permeable motif composed of total 9 amino acid sequences derived from a protein transduction domain contained in TAT of human immunodeficiency virus (HIV).

The amino acid sequence represented by SEQ ID NO: 24 corresponds to a membrane-permeable motif composed of total 11 amino acid sequences of a protein transduction domain (PTD4) obtained by modifying above-mentioned TAT The amino acid sequence represented by SEQ ID NO: 25 corresponds to a membrane-permeable motif composed of total 18 amino acid sequences derived from Antennapedia complex ANT, a mutant of *Drosophila*.

Among these, amino acid sequences related to an NoLS and TAT (or modified amino acid sequences thereof) are particularly preferable. For example, an NoLS-related CPP sequence as represented by SEQ ID NO: 21 or SEQ ID NO: 22 and TAT- or ANT-related CPP sequences represented by SEQ ID NOS: 23 to 25 can be preferably used to construct the antitumor peptide disclosed herein.

As was previously described, as the peptide chain (amino acid sequence) of the antitumor peptide disclosed herein, any one may be used as long as it includes followings:

(1) an amino acid sequence composing the second TM region from the N-terminal of S1PR1 or above-mentioned modified amino acid sequence hereinafter, also referred to as "S1PR1-TM2-related sequence"; and (2) an amino acid sequence functioning as a CPP (hereinafter, also referred to as a "CPP-related sequence"), wherein either of the S1PR1-TM2-related sequence and the CPP-related sequence are arranged relatively on the N-terminal side (or C-terminal side).

The S1PR1-TM2-related sequence and CPP-related sequence are preferably arranged directly adjacent to each other, and more specifically, and amino acid residues not included in both sequence portions are preferably not present between the S1PR1-TM2-related sequence and the CPP-related sequence. Alternatively, even if present, the number of amino acid residues functioning as a linker connecting above-mentioned 2 sequences are preferably 10 or less (and more preferably 5 or less, such as 1 or 2 amino acid residues).

Sequence portions (amino acid residues) other than the amino acid sequences that compose the S1PR1-TM2-related sequence and CPP-related sequence can be contained as long as there is no loss of antitumor activity capable of suppressing proliferation of at least one type of tumor cells.

The antitumor peptide disclosed herein is such that the total number of amino acid residues that compose the peptide chain is suitably 100 or less, preferably 80 or less and preferably 70 or less (such as a peptide chain consisting of about 30 to about 50 amino acid residues). A short peptide having such a chain length can be obtained easily by chemical synthesis and can easily provide an antitumor peptide. A linear or helical peptide chain is preferable from the viewpoint of having difficulty in becoming an immunogen (antigen), although not particularly limited thereto. A peptide having such form has difficulty in composing epitopes.

The proportion of the S1PR1-TM2-related sequence and the CPP-related sequence in the entire amino acid sequence of the synthesized peptide is roughly 80% or more and preferably 90% or more although not limited thereto as long as antitumor activity is not lost. Furthermore, although all amino acid residues are preferably those of L-amino acids, a portion or all of the amino acid residues may be substituted with D-amino acids as long as antitumor activity is not lost.

Preferably, the antitumor peptide disclosed herein is preferably such that at least one amino acid residue is amidated. Amidation of carboxyl group of an amino acid residue (and typically the C-terminal amino acid residue of the peptide chain) improves structural stability of the synthetic peptide (such as by improving protease resistance). For example, when the C-terminal of the antitumor peptide composes the CPP-related sequence portion, the C-terminal amino acid residue of that sequence portion is preferably amidated. Meanwhile, when the C-terminal of the antitumor peptide composes the 51PR1-TM2-related sequence portion, the C-terminal amino acid residue of that sequence portion is preferably amidated. In another preferable aspect, stability of a synthetic peptide can be improved by amidating the C-terminal amino acid residue of a synthetic peptide having the amino acid sequence represented by SEQ ID NO: 27 or SEQ ID NO: 33.

The antitumor peptide disclosed herein can be easily produced in compliance with ordinary chemical synthesis methods. For example, a conventionally known solid-phase synthesis method or liquid-phase synthesis method may be employed. A solid-phase synthesis method that applies a t-butyloxycarbonyl (Boc) group or 9-fluorenylmethoxycarbonyl (Fmoc) group as a protecting group of an amino group is preferable.

The antitumor peptide disclosed herein can be obtained by synthesizing a peptide chain having a desired amino acid sequence of modified portion (such as amidation of the C-terminal) using a solid-phase synthesis method that uses a commercially available peptide synthesizer.

Alternatively, the antitumor peptide may also be biosynthesized based on genetic engineering techniques. Namely, a polynucleotide (typically, DNA) of a nucleotide sequence (that contains an ATG start codon) encoding the amino acid sequence of the desired antitumor peptide is synthesized. A recombinant vector having an expression gene construct composed of the synthesized polynucleotide (DNA) and various regulatory elements for expressing the amino acid sequence in host cells (including a promoter, ribosome binding site, terminator, enhancer, and various cis-elements controlling expression level) is constructed corresponding to the host cells.

This recombinant vector is then introduced into prescribed host cells (such as yeast, insect cells or animal cells) using an ordinary method followed by culturing the host cells, or culturing tissue or an individual containing the cells, under prescribed conditions. As a result, the target peptide can be expressed and produced in the cells. The peptide can then be isolated from the host cells (or culture medium in the case of being secreted therein) followed by refolding or purification as necessary to obtain the target antitumor peptide.

Furthermore, a conventional method carried out in the art may be employed as is for constructing the recombinant vector and introducing the recombinant vector into the host cells, and detailed explanation thereof is omitted since such method per se does not particularly characterize the present invention.

Alternatively, a target polypeptide can be synthesized in vitro by employing a so-called cell-free protein synthesis system by constructing template DNA for the cell-free protein synthesis system (namely, a synthetic gene fragment containing a nucleotide sequence that encodes the amino acid sequence of the antitumor peptide) and using various compounds required for peptide synthesis (such as ATP, RNA polymerase and amino acids). Examples of the literature that can be referred to with regard to cell-free protein synthesis systems include the report by Shimizu, et al. (Shimizu, et al., Nature Biotechnology, 19, 751-755 (2001)) and the report by Madin et al. (Madin, et al., Proc. Natl. Acad. Sci., USA, 97(2), 559-564 (2000)). Numerous private corporations have already been commission with production of polypeptides based on the technologies described in these reports at the time of filing of the present application, and cell-free protein synthesis kits are available commercially (such as that available from CellFree Sciences Co., Ltd., Japan).

A nucleotide sequence encoding the antitumor peptide disclosed herein and/or a single-stranded or double-stranded polynucleotide containing a nucleotide sequence complementary to that sequence can be easily produced (synthesized) according to a conventionally known method. Namely, a nucleotide sequence corresponding to the amino acid sequence of the antitumor peptide is easily determined and provided by selecting a codon corresponding to each amino acid residue composing the designed amino acid sequence. Once the nucleotide sequence has been determined, a polynucleotide (single-stranded) corresponding to the desired nucleotide sequence can be easily obtained using a DNA synthesizer and the like. The target double-stranded DNA can be further obtained by using the resulting single-stranded DNA as a template and employing various enzymatic synthesis means (typically, PCR). In addition, the polynucleotide may be DNA or RNA (mRNA, etc.). DNA can be provided as a double strand or single strand. In the case of being provided as a single strand, it may be a coding strand (sense strand) or non-coding strand (antisense strand) of a sequence complementary thereto.

As was previously described, the polynucleotide obtained in this manner can be used as a material for constructing a recombinant gene (expression cassette) for producing the antitumor peptide in various host cells or with a cell-free protein synthesis system.

The antitumor peptide disclosed herein can be preferably used as an active ingredient of composition used in applications for suppressing (or inhibiting) proliferation of tumor cells (namely, a pharmaceutical antitumor composition such as an antitumor drug). Furthermore, the antitumor peptide may also be salt provided the antitumor activity thereof is not lost. For example, acid addition salt of a synthetic peptide obtainable by addition reaction of an ordinarily used inorganic acid or organic acid can be used in accordance with ordinary methods. Thus, the term "peptide" as described in the present description and claims includes such salt forms.

The antitumor composition disclosed herein can contain various pharmacologically (pharmaceutically) acceptable carriers corresponding to usage form thereof as long as the antitumor activity of the active ingredient in the form of the antitumor peptide is not lost. For example, carriers commonly used in peptide pharmaceuticals can be applied as diluents or excipients and the like.

Although the type of such pharmacologically (pharmaceutically) acceptable carrier depends on application or form of the antitumor composition disclosed herein, typical examples of such carriers include water, physiological buffers and various organic solvents. Aqueous solutions of alcohol (such as ethanol) having suitable concentration, glycerol and non-drying oils such as olive oil can also be used. Alternatively, liposomes may also be used as the carrier. In addition, examples of secondary components able to be contained in the antitumor composition include various fillers, extenders, binders, humectants, surfactants, pigments and fragrances.

Examples of typical forms of the antitumor composition (antitumor drug) include liquid, suspension, emulsion, aerosol, foam, granules, powder, tablets, capsules, ointment and aqueous gel. In addition, the antitumor composition may also be a freeze-dried product or granulated substance for preparing a liquid preparation by dissolving in physiological saline or suitable buffer (such as PBS) immediately prior to use in order to use in an injection preparation and the like.

Furthermore, the process per se for preparing various forms of compositions (drugs) by using the antitumor peptide (primary component) and various carriers (secondary components) as materials thereof are in compliance with conventionally known methods, and detailed explanation of production method per se is omitted since it does not characterize the present invention. An example of a source of detailed information relating to formulation is Comprehensive Medicinal Chemistry, Corwin Hansch, ed., Pergamon Press, pub. (1990). The entire contents of this publication are incorporated in the present description by reference.

There is no particular limitation on the applicable cells of the antitumor composition (antitumor peptide) disclosed herein as long as they are tumor cells (cancer cells), and various types of tumor cells formed in humans or mammals other than humans. For example, numerous types of squamous cell carcinomas and adenocarcinomas are included. Other examples include cancer cells of kidney cancer, prostate cancer, melanoma and lung cancer (such as non-small cell lung cancer, small cell lung cancer or alveolar epithelial cell carcinoma) and/or cells composing breast cancer, colon cancer, pancreatic cancer, skin cancer such as basal cell carcinoma, neuroblastoma, retinoblastoma, pheochromocytoma and other cytomas.

The antitumor composition disclosed herein can be used according to methods and doses corresponding to the form and purpose thereof in the same manner as conventional peptide preparation. For example, the antitumor composition can be administered in a desired amount to the affected area (typically, malignant tumor tissue) of a patient (namely, a body) by injecting intravenously, intramuscularly, subcutaneously, intradermally or intraperitoneally as liquid. Alternatively, that in solid form such as tablet, gel or aqueous jelly such as an ointment can be administered directly to prescribed tissue (namely, affected areas such as tissue or organ containing tumor cells). Alternatively, that in solid form such as tablet can be administered orally. In the case of oral administration, encapsulation or the application of a protective (coating) material is preferable in order to prevent decomposition by digestive enzymes in digestive tract.

Alternatively, suitable amount of the antitumor composition disclosed herein (namely, a suitable amount of the antitumor peptide) is supplied at least once to a medium of target cultured cells (such as tissue) for tumor cells (including cultured cell lines or cells, tissues or organs extracted from body) cultured outside body (in vitro). Although there is no particular limitation on supplied amount each time and supplied times since they can vary according to condition such as type of cultured tumor cells, cell density (cell density at start of culturing), passage number, culturing conditions or medium concentration, the antitumor composition is preferably added once, twice or more times so that the concentration of antitumor peptide in the medium is generally within range of 5 μM to 100 μM and preferably within range of 10 μM to 50 μM (such as 12.5 μM to 25 μM).

Although there is no particular limitation on the method used to test antitumor activity of the antitumor composition disclosed herein in vitro, an example of a preferable test consists of the use of a reagent for measuring cell proliferation that uses tetrazolium salt. In a preferable aspect thereof, cell proliferation rate (or cell viability) calculated in this test for the addition of the antitumor composition disclosed herein versus a comparative example in which the antitumor composition is not added is lower than 30% (preferably lower than 20% and more preferably lower than 10%).

Although the following provides explanation of several examples relating to the present invention, these examples are not intended to limit the present invention to that indicated in the examples.

Test Example 1: Peptide Synthesis

The 7 types of peptides shown in Table 1 were produced using a commercially available peptide synthesizer. The detail thereof is as indicated below.

Sample 1 (SEQ ID NO: 26) is a synthetic peptide designed as an example that contains the amino acid sequence represented by SEQ ID NO: 21 (NoLS of LIM kinase 2) as a CPP-related sequence on the C-terminal of the amino acid sequence of the first TM region from the N-terminal of human S1PR1 (SEQ ID NO: 1).

Sample 2 (SEQ ID NO: 27) is a synthetic peptide designed as an example that contains the amino acid sequence represented by SEQ ID NO: 21 (NoLS of LIM kinase 2) as a CPP-related sequence on the C-terminal of the amino acid sequence of the second TM region from the N-terminal of human S1PR1 (SEQ ID NO: 2).

Sample 3 (SEQ ID NO: 28) is a synthetic peptide designed as an example that contains the amino acid sequence represented by SEQ ID NO: 21 (NoLS of LIM kinase 2) as a CPP-related sequence on the C-terminal of the amino acid sequence of the third TM region from the N-terminal of human S1PR1 (SEQ ID NO: 3).

Sample 4 (SEQ ID NO: 29) is a synthetic peptide designed as an example that contains the amino acid sequence represented by SEQ ID NO: 21 (NoLS of LIM kinase 2) as a CPP-related sequence on the C-terminal of the amino acid sequence of the fourth TM region from the N-terminal of human S1PR1 (SEQ ID NO: 4).

Sample 5 (SEQ ID NO: 30) is a synthetic peptide designed as an example that contains the amino acid sequence represented by SEQ ID NO: 21 (NoLS of LIM kinase 2) as a CPP-related sequence on the C-terminal side of the amino acid sequence of the fifth TM region from the N-terminal of human S1PR1 (SEQ ID NO: 5).

Sample 6 (SEQ ID NO: 31) is a synthetic peptide designed as an example that contains the amino acid sequence represented by SEQ ID NO: 21 (NoLS of LIM kinase 2) as a CPP-related sequence on the C-terminal side of the amino acid sequence of the sixth TM region from the N-terminal of human S1PR1 (SEQ ID NO: 6).

Sample 7 (SEQ ID NO: 32) is a synthetic peptide designed as an example that contains the amino acid sequence represented by SEQ ID NO: 21 (NoLS of LIM kinase 2) as a CPP-related sequence on the C-terminal side of the amino acid sequence of the seventh TM region from the N-terminal of human S1PR1 (SEQ ID NO: 7).

CAKI2 cells were cultured and adjusted to cell count of about $5 \times 10^3$ cells per single well of 96-well plate. The amount of medium at this time was made to be 100 μL per well.

Next, the 96-well plate was arranged in a $CO_2$ incubator and incubated for about 1 day (21 hours to 24 hours) under conditions of 37° C. and 5% $CO_2$.

Subsequently, peptide-containing test media were respectively prepared for each concentration so that the concentration of each sample peptide targeted for evaluation was 12.5 μM and 25 μM followed by supplying to the wells in which the cells targeted for evaluation were cultured (namely, the wells following the above-mentioned incubation) so that the amount of media was 90 μL per well. The 96-well plate was then returned to $CO_2$ incubator followed by incubating for 48 hours under conditions of 37° C. and 5% $CO_2$.

The number of wells (n) at each concentration in each peptide addition test group was set to 3. Thus, the values of the results indicated in the following table are the average values of the results respectively obtained for 3 test wells. Cell viability (%) was determined in the manner described below.

TABLE 1

| Sample No. | Amino Acid Sequence | Total No. of Amino Acid Residues | SEQ ID NO: |
|---|---|---|---|
| 1 | LTSVVFILICCFHLENIFVLLKKRTLRKNDRKKR-$CONH_2$ | 35 | 26 |
| 2 | FIGNLALSDLLAGVAYTANLLLKKRTLRKNDRKKR-$CONH_2$ | 35 | 27 |
| 3 | WFLREGSMFVALSASVFSLLAIKKRTLRKNDRKKR-$CONH_2$ | 35 | 28 |
| 4 | FLLISACWVISLILGGLPIMGWKKRTLRKNDRKKR-$CONH_2$ | 35 | 29 |
| 5 | LYHKHYILECTTVFTLLLLSIVILYCRIKKRTLRKNDRKKR-$CONH_2$ | 41 | 30 |
| 6 | VIIVLSVFIACWAPLFILLLLKKRTLRKNDRKKR-$CONH_2$ | 34 | 31 |
| 7 | LFRAEYFLVLAVLNSGTNPIIKKRTLRKNDRKKR-$CONH_2$ | 34 | 32 |

Each of the peptides of above-mentioned Samples 1 to 7 was synthesized carrying out a solid-phase synthesis method (Fmoc method) according to the manual using a commercially available peptide synthesizer. Furthermore, since the manner of use per se of the peptide synthesizer does not characterize the present invention, detailed explanation thereof is omitted. Furthermore, all synthetic peptides listed in Table 1 are such that the carboxyl group (—COOH) of the C-terminal amino acid in the peptide having the amino acid sequence of the corresponding sequence ID number is amidated (—$CONH_2$).

The synthesized peptide of each sample was dissolved in dimethylsulfoxide (DMSO) to prepare a stock solution (concentration: 2.5 mM) of each sample peptide.

Test Example 2: Evaluation Test of Antitumor Activity of Each Synthetic Peptide (1)

The antitumor activity of each sample peptide synthesized in above-mentioned Test Example 1 was evaluated targeted in human-derived cultured tumor cells.

More specifically, a human kidney cancer cell line (CAKI2) that is currently commercially available was used for the test tumor cells.

The details of the test are as indicated below.

Following completion of incubation for 48 hours as described above, the medium in each well was replaced with 100 μL of fresh medium not containing peptide followed by further adding a reagent for measuring cell proliferation in the form of "Cell Counting Kit-8" (Dojindo Laboratories) containing "water-soluble tetrazolium salt (WST-8)" as a coloring reagent at 10 μL per well. Subsequently, the 96-well plate was again returned to $CO_2$ incubator and incubated for 1.5 hours to 2 hours under conditions of 37° C. and 5% $CO_2$.

Following completion of incubation, cell viability (%) was evaluated using a colorimetric method consisting of recovering the cell culture liquid containing the above-mentioned reagent together with measuring absorbance at wavelength of 450 nm based on reduction of tetrazolium salt (value corrected for absorbance at a wavelength of 650 nm: A450 to A650). More specifically, the cell viability (%) of each test cell line was calculated from the measured absorbance as a relative value based on cell viability of 100% for the measured value (measured absorbance) of the comparison test group that underwent incubation for 48 hours as described above in only medium not containing peptide. The results are shown in Table 2.

As is clear from the results shown in Table 2, superior antitumor activity (tumor cell proliferation inhibitory activity) was observed for CAKI2 cells in the case of Sample 2 only.

TABLE 2

| Test Cell Line | Peptide Concentration (μM) | Cell Viability (%) Sample Peptide No. | | | | | | |
|---|---|---|---|---|---|---|---|---|
| | | No. 1 | No. 2 | No. 3 | No. 4 | No. 5 | No. 6 | No. 7 |
| Kidney Cancer Cells (CAKI2) | 12.5 | 49.6 | 9.2 | 68 | 70.6 | 73.3 | 69.3 | 98.9 |
| | 25 | 48 | 0.4 | 45.8 | 85.6 | 77.6 | 59.7 | 66.3 |

Test Example 3: Evaluation Test of Antitumor Activity of Each Synthetic Peptide (2)

Antitumor activity was evaluated for Sample 2 in above-mentioned Test Example 1 targeted at multiple types of human-derived cultured tumor cells.

More specifically, human kidney cancer cell line (CAKI2), human prostate cancer cell line (PC-3), human melanoma cell line (A2058), human non-small cell lung cancer cell line (NCI-H2444) and human alveolar epithelial cell carcinoma cell line (A549), which are currently commercially available, were used for the test tumor cells. In addition, a culture of normal human mammary epithelial cells (MCF-12F) was used for comparison.

The following media were used to culture each of the cell lines.

(1) Human kidney cancer cell line (CAKI2):
McCoy's 5A medium (Gibco) containing 2 mM L-glutamine, 3,000 mg/L of glucose, 100 units/mL of penicillin, 100 μg/mL of streptomycin and 10% fetal bovine serum (FBS).

(2) Human prostate cancer cell line (PC-3):
Ham's F12K medium (Wako Pure Chemical Industries, Ltd.) containing 2 mM L-glutamine, 1 mM sodium pyruvate, 100 units/mL of penicillin, 100 μg/mL of streptomycin and 10% FBS.

(3) Human non-small cell lung cancer cell line (NCI-H2444) and human alveolar basal epithelial adenoma cell line (A549):
RPMI-1640 medium (Wako Pure Chemical Industries, Ltd.) containing 2 mM L-glutamine, 1 mM sodium pyruvate, 10 mM HEPES, 4,500 mg/mL of glucose, 100 units/mL of penicillin, 100 μg/mL of streptomycin and 10% FBS.

(4) Human melanoma cell line (A2058):
DMEM medium (Wako Pure Chemical Industries, Ltd.) containing 2 mM L-glutamine, 0.1 mM non-essential amino acids, 100 units/mL of penicillin, 100 μg/mL of streptomycin and 10% FBS.

(5) Culture of normal human mammary epithelial cells (MCF-12F):
DMEM/F12 medium (Wako Pure Chemical Industries, Ltd.) containing 20 ng/mL of recombinant EGF, 10 μg/mL of insulin, 0.5 μg/mL of hydrocortisone and 10% FBS.

Details of the test are as described in Test Example 1. The results are shown in Table 3.

As is clear from the results shown in Table 3, the above-mentioned synthetic peptides of Sample 2 were all observed to have more potent antitumor activity against each of the tumor cells used in this test example in comparison with the culture of normal human mammary epithelial cells (MCF-12F) used for comparison. This indicates that the antitumor peptide disclosed herein is able to suppress proliferation of tumor cells in a manner that is specific to each of the tumor cells.

TABLE 3

| Test Cell Line | Peptide Concentration (μM) | Cell Viability (%) |
|---|---|---|
| Kidney Cancer Cell (CAKI2) | 12.5 | 9.2 |
| | 25 | 0.4 |
| Prostate Cancer Cell (PC-3) | 12.5 | 25.6 |
| | 25 | 2.5 |
| Melanoma (A2058) | 12.5 | 6.5 |
| | 25 | 0.2 |
| Lung Cancer Cell (H2444) | 12.5 | 11 |
| | 25 | 0.6 |
| Human Alveolar Basal Epithelial Adenoma Cell (A549) | 12.5 | 25.4 |
| | 25 | 1.4 |
| Normal Human Mammary Epithelial Cell (MCF-12F) | 12.5 | 59.6 |
| | 25 | 13.8 |

Although detailed data is not shown, Sample 2 was also observed to demonstrate similar antitumor activity against cultured tumor cell lines derived from several species of mammals (such as mice) other than humans. This indicated the usefulness of a synthetic peptide provided with both S1PR1-TM2-related sequence and CPP-related sequence as an antitumor peptide.

In addition, although the detailed data is not shown, a synthetic peptide (SEQ ID NO: 33) having an amino acid sequence obtained by binding the amino acid sequence represented by SEQ ID NO: 23, which is TAT sequence of HIV, to the C-terminal side of the amino acid sequence represented by SEQ ID NO: 2 also demonstrated antitumor activity. This indicated that the S1PR1-TM2-related sequence is useful as an antitumor peptide independent of the amino acid sequence of the CPP-related sequence bound thereto.

As was previously described, according to the antitumor peptide disclosed herein, proliferation of tumor cells can be suppressed (or inhibited). Consequently, use of the antitumor peptide provided by the present invention makes it possible to provide an antitumor composition (antitumor drug) suppressing proliferation of at least one type of tumor cells.

The invention claimed is:

1. A synthetic peptide for suppressing proliferation of at least one type of tumor cell, the synthetic peptide comprising both of the amino acid sequences indicated in the following (1) and (2):
   (1) an amino acid sequence comprising the amino acid sequence of SEQ ID NO: 2; and
   (2) an amino acid sequence functioning as a cell-penetrating peptide (CPP), wherein the amino acid sequence functioning as the cell-penetrating peptide (CPP) is represented by any one of SEQ ID NOS: 8 to 25;
   wherein:
   the total number of amino acid residues of the synthetic peptide is 100 or less;
   the amino acid sequence functioning as a cell-penetrating peptide (CPP) is directly attached to N-terminal Phe or C-terminal Lys, or both, of the amino acid seqluence of SEQ ID NO: 2; and
   the at least one type of tumor cell is selected from a kidney cancer cell, a prostate cancer cell, a melanoma cell, a lung cancer cell, or a breast cancer cell.

2. The synthetic peptide according to claim 1, having the amino acid sequence represented by SEQ ID NO: 27 or SEQ ID NO: 33.

3. An antitumor composition for suppressing proliferation of at least one type of cancer cell, comprising:
   a synthetic peptide; and
   at least one pharmacologically acceptable carrier,
   wherein the synthetic peptide comprises both of the amino acid sequences indicated in the following (1) and (2):
   (1) an amino acid sequence comprising the amino acid sequence of SEQ ID NO: 2; and
   (2) an amino acid sequence functioning as a cell-penetrating peptide (CPP), wherein the amino acid sequence functioning as the cell-penetrating peptide (CPP) is represented by any one of SEQ ID NOS: 8 to 25; and
   wherein:
   the total number of amino acid residues of the synthetic peptide is 100 or less;
   the amino acid sequence functioning as a cell-penetrating peptide (CPP) is directly attached to N-terminal Phe or C-terminal Lys, or both, of the amino acid seqluence of SEQ ID NO: 2; and
   the at least one type of cancer cell is selected from a kidney cancer cell, a prostate cancer cell, a melanoma cell, a lung cancer cell, or a breast cancer cell.

4. The antitumor composition according to claim 3, wherein the synthetic peptide has the amino acid sequence represented by SEQ ID NO: 27 or SEQ ID NO: 33.

* * * * *